United States Patent
Yagyu

(10) Patent No.: US 10,280,384 B2
(45) Date of Patent: May 7, 2019

(54) EXTRACTED OLIVE OIL AND PRODUCTION METHOD THEREOF

(71) Applicant: SHODOSHIMA HEALTHY LAND CO., LTD., Shouzu-gun (JP)

(72) Inventor: Yoshihiko Yagyu, Shozu-gun (JP)

(73) Assignee: SHODOSHIMA HEALTHY LAND CO., LTD., Kagawa (JP)

( * ) Notice: Subject to any disclaimer, the term of this patent is extended or adjusted under 35 U.S.C. 154(b) by 22 days.

(21) Appl. No.: 14/203,324

(22) Filed: Mar. 10, 2014

(65) Prior Publication Data

US 2014/0194606 A1  Jul. 10, 2014

Related U.S. Application Data

(63) Continuation of application No. 12/385,402, filed on Apr. 7, 2009, now abandoned.

(51) Int. Cl.
| | |
|---|---|
| C11B 1/02 | (2006.01) |
| C11B 1/04 | (2006.01) |
| C11B 9/02 | (2006.01) |
| A61K 36/63 | (2006.01) |

(52) U.S. Cl.
CPC .............. C11B 9/02 (2013.01); A61K 36/63 (2013.01); C11B 1/025 (2013.01); C11B 1/04 (2013.01)

(58) Field of Classification Search
CPC ........... A61K 36/63; C11B 1/025; C11B 1/04; C11B 9/02
See application file for complete search history.

(56) References Cited

U.S. PATENT DOCUMENTS

| | | | |
|---|---|---|---|
| 6,338,865 B1 | 1/2002 | Van Putte | |
| 7,687,248 B2 * | 3/2010 | King | C08B 30/042 426/549 |
| 7,879,584 B2 * | 2/2011 | Rama Krishna | C11B 9/02 435/132 |
| 7,883,884 B2 * | 2/2011 | Bonde | A01C 3/00 435/236 |
| 8,841,101 B2 * | 9/2014 | Medoff | A61K 8/97 435/171 |
| 9,725,695 B2 * | 8/2017 | Muotri | C12N 5/0606 |
| 9,861,677 B2 * | 1/2018 | Antony | A61K 36/9066 |
| 10,016,528 B2 * | 7/2018 | Rosines | A61L 27/3612 |
| 10,028,970 B2 * | 7/2018 | Chapal | A61K 36/22 |
| 2010/0255133 A1 | 10/2010 | Yagyu | |

FOREIGN PATENT DOCUMENTS

| | | |
|---|---|---|
| JP | A-9-78061 | 3/1997 |
| JP | A-2000-96077 | 4/2000 |
| JP | A2004-307709 | * 11/2004 |
| JP | A-2004-307709 | 11/2004 |
| JP | 3937228 B2 * | 6/2007 |
| JP | B2-3937228 | 6/2007 |

OTHER PUBLICATIONS

Patteson, J. Beauty Tips From the Gladiators; Olive Oil is Being Worked Into New Cosmetics; Toronto Star; Ontario, Canada, Jul. 26, 2001, p. E07 (pp. 1-2 of ProQuest.*
The Olive Oil Source, online, URL http://www.oliveoilsource.com/page/chemical-characteristics> accessed Apr. 6, 2012, pp. 1-5.*
Giovacchino et al.: Effect of Mixing Leaves With Olives on Organoleptic Quality of Oil Obtained by Centrifugation; JAOCS, vol. 73, No. 3 (1996).*
Battcock et al. Fermented Fruits and Vegetables: A Global Perspective; Chapter 5, Bacterial Fermentations; Agricultural Services Bulletin No. 134, Food and Agriculture Organization of the United Nations Rome 1998, 12 pages printed from the internet, Online, URL< http://www.fao.org/docrep/x0560e/x0560e10.htm >.*
Randazzo et al, Olives and Olive Oil in Health and Disease Prevention, Elsevier (V.R. Preedy and R.R.Watson Ed.), pub. online Mar. 17, 2010, chapter 41 Abstract only, 2 pages. ISBN: 978-0-12-374420-3; doi: 10.1016/B978-0-12-374420-3.00041-3.*
Genovese, . et al "Olive oil phenolic compounds affect the release of aroma compounds" Food Chemistry 181 (2015) 284-294. doi: 10.1016/j.foodchem.2015.02.097.*
Angerosa F, et al "Volatile compounds in virgin olive oil: occurrence and their relationship with the quality" J. Chromat. A, Oct. 29, 2004, 1054(1-2), pp. 17-31: doi:10.1016/j.chroma.2004.07.093 (Year: 2004).*
Vossen, Paul; Kicenik Devarenne Alexandra "UC Cooperative Extension sensory analysis panel enhances the quality of California olive oil" California Agriculture, Jan.-Mar. 2011, 65(1), p. 8-13. (Year: 2011).*
Di Giovacchino et al., "Effect of Mixing Leaves with Olives on Organoleptic Quality of Oil Obtained by Centrifugation," *Journal of the American Oil Chemists' Society*, vol. 73, No. 3, Jan. 1, 1996, pp. 371-374.
Kiritsakis, "Flavor Components of Olive Oil—A Review," *Journal of the American Oil Chemists' Society*, vol. 75, No. 6, 1998, pp. 673-681.
U.S. Appl. No. 12/385,402, filed Apr. 7, 2009, Yoshihiko Yagyu.

* cited by examiner

*Primary Examiner* — Aaron J Kosar
(74) *Attorney, Agent, or Firm* — Oliff PLC

(57) ABSTRACT

Extracted olive oil having extremely less olive smell and excellent skin permeability, and having an extremely higher antioxidative property than that of common olive oil. Also provided is a method for producing extracted olive oil including: crushing olive fruits and olive leaves; and producing the extracted olive oil from an obtained paste-like matter, where the olive fruits and the olive leaves are lactic fermented before or after the crushing step or during the crushing step.

15 Claims, 1 Drawing Sheet

EXTRACTED OLIVE OIL AND PRODUCTION METHOD THEREOF

This application is a continuation of application Ser. No. 12/385,402, filed Apr. 7, 2009, the contents of which are incorporated herein by reference in their entirety.

DETAILED DESCRIPTION OF THE INVENTION

Technical Field

The present invention relates to a production method of extracted olive oil having no olive smell and having excellent skin permeability and a high antioxidative property, and extracted olive oil produced by the method.

Related Art

Olive oil is a vegetable oil containing various active ingredients such as oleic acid, provitamin A, vitamin B, vitamin Ks, and polyphenols, and has recently attracted attention regarding its effect of improving health conditions. Especially, olive oil has been reported to have the effect of suppressing cancer generation based on vitamin Ks and polyphenols, and the effect of facilitating bone formation based on provitamin A, vitamin D, and vitamin K. Moreover, olive oil has effects of improving the skin, such as reducing skin roughness, keeping the skin healthy, moisturizing the skin, protecting the skin, and preventing dry skin, and has been compounded in cosmetics, medicines for external use, and the like.

Olive oil production methods have been improved in order to increase the yield point and to obtain as much oil as possible from olives. In addition to cold pressing having a yield of 25% to 30%, a chemical extraction method achieving a higher yield has been developed. In these methods, the chemical extraction method requires an organic solvent added during production to be removed for refining by means such as distillation, but at this time, active ingredients contained in olive oil may also be removed. Moreover, heating which is conducted during refining of olive oil changes a cis fatty acid, which is effective to improve health conditions, into a trans fatty acid, thereby reducing usefulness of the olive oil.

In recent years, as the active ingredients contained in olive oil has become increasingly clear, the focus has been placed on producing olive oil without denaturing the active ingredients. An olive oil production method suitable for this purpose is cold pressing, in which olive fruits are mechanically crushed, and then pressed at ordinary temperature without preheating to obtain olive oil. Especially, in the pressing process as well, the temperature in a pressing machine is controlled so as not to exceed 65 to 75° C. The olive oil thus produced contains non-denatured active ingredients described above, and change of the fatty acid does not occur.

Moreover, a production method including the steps of (a) bringing mixed oil of olive residue oil obtained by solvent-extracting an olive fruit residue remaining after collecting olive oil and olive oil obtained by pressing olive fruits into contact with an adsorbent, (b) separating and removing the adsorbent to bleach the mixed oil, and (c) removing an odorant from the bleached mixed oil by distillation means has been reported as a production method of olive oil suitable as frying oil (see, e.g., Japanese Patent Application Publication No. JP-A-2000-960707). The olive oil obtained by the above production method has improved heat stability, oxidation stability, and preservation stability, and can be preferably used for frying.

Problem to be Solved by the Invention

By the way, as olive oil has been increasingly used for things other than food, a distinctive aroma of olive has become an issue in recent years. Such olive smell is preferable when olive oil is used in food, but when olive oil is used in cosmetics, medicines for external use, and the like, it cannot be said that the olive smell is preferable. Rather, the olive smell has been avoided as under-ripe smell. Especially in compounds containing a perfume as an additive, the olive smell may interfere with the added perfume, causing bad smell.

Moreover, olive oil does not have so high skin permeability when applied to the skin, and the olive oil which does not permeate the skin remains on the skin surface, causing stickiness on the skin. The skin-improving effects of olive oil preferably appear when the olive oil is applied directly to the skin. Therefore, there has been a demand to improve the skin permeability of olive oil.

In view of the above problems, the inventor found that extracted olive oil having less olive smell and excellent skin permeability can be produced by subjecting harvested and sorted olive fruits to lactic fermentation (Japanese Patent No. 3937228).

It is an object of the present invention to provide extracted olive oil having extremely less olive smell and excellent skin permeability, and having an extremely higher antioxidative property than that of common olive oil. Moreover, it is an object of the present invention to provide a method capable of producing such extracted olive oil by simpler operation.

Means for Solving the Problem

As a result of keen studies, the inventor found that, surprisingly enough, extracted olive oil having reduced olive smell and, rather, having sweet and sour fruity smell can be produced by mixing olive leaves with olive fruits before pressing oil, and fermenting the mixture under prescribed conditions in a production method of extracted olive oil including the steps of crushing olive fruits and separating oil. Moreover, it was found that this extracted olive oil has excellent skin permeability and also an extremely high antioxidant property. The present invention was completed based on these findings.

Accordingly, the present invention is a method for producing extracted olive oil by crushing olive fruits and olive leaves and producing the extracted olive oil from an obtained paste-like matter, characterized in that the olive fruits and the olive leaves are lactic fermented before or after the crushing step or during the crushing step.

Preferred forms of the above production method of the extracted olive oil are as follows:
- The above production method, wherein the fermentation is continued until olive smell generated by the olive fruits changes to fruity smell;
- The above production method, wherein an amount of the olive leaves is 0.1 to 10% based on a total weight of the olive fruits and the olive leaves;
- The above production method, wherein the fermentation is performed by immersing the olive fruits and the olive leaves in saline water; and
- The above production method, wherein the saline water has a concentration of 1 to 10%.

The present invention further relates to extracted olive oil produced by the above method of the present invention.

Effects of the Invention

In the production method of the present invention, extracted olive oil having less olive smell and having pleasant fruity smell, and having an excellent antioxidant property and high preservation stability can be produced by simple operation by fermenting fruits together with leaves under prescribed conditions before pressing oil from the olive fruits. This extracted olive oil has high skin permeability, and is rapidly absorbed and does not cause stickiness when applied. Accordingly, the extracted olive oil obtained by the production method of the present invention is suitably compounded in cosmetics, medicines for external use, and the like intended to provide the effects obtained by olive oil, especially, the skin-improving effects.

EMBODIMENT OF THE INVENTION

Hereinafter, the present invention will be described in more detail with reference to the accompanying drawings.

Figure 1:
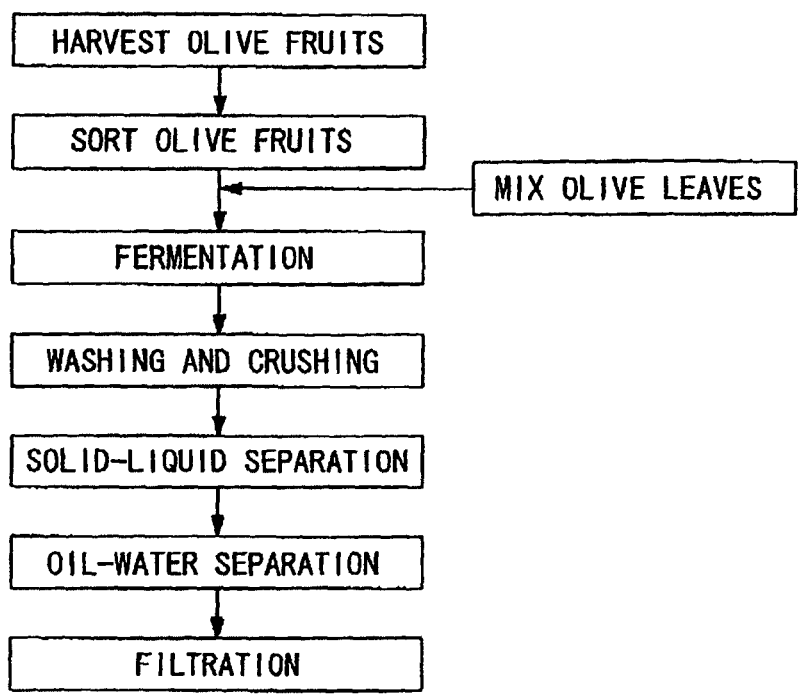
FIG. 1 is a flowchart showing an example of a production method of extracted olive oil according to the present invention.

FIG. 1 is a flowchart showing an example of a production method of extracted olive oil according to the present invention. Hereinafter, each step of the production method of extracted olive oil of the present invention will be described with reference to FIG. 1.

In the production method of the present invention, olive fruits, which will be a material of extracted olive oil, are first harvested. There are various species of olive. For example, Mission, Manzanillo, Nevadilo Blanco, Picual, Hojiblanca, Arbequina, Cornicabra, Manzanilla, Gordal, Frantoio, Moraiolo, Leccino, Coratina, Ascolana Terena, Oliviere, FS17, Lucca, Koroneiki, and the like are known. These species of olive have different average fruit weights and different oil contents, and their suitable usages are different, such as species for fruit processing, species for oil, and species for both purposes, and the like. The extracted olive oil of the present invention can be produced from any species of olive. The harvest time of olive fruits is preferably around December when olive fruits get to have a high oil content, and it is preferable to use fully ripened olive fruits.

Next, the harvested olive fruits are sorted. Sorting is performed in order to prevent degradation of characteristics of the produced extracted olive oil due to mixing of sick fruits and unripe fruits. Typically, defective fruits are selected visually, and removed by hand.

Conventionally, care needed to be taken so that olive leaves are not mixed during the above harvest and sorting of the olive fruits, and if mixed, a process of removing the olive leaves was required. In the case of the present invention, however, it is not necessary to avoid mixing of the leaves, whereby the harvesting and sorting processes are simplified.

The mixing amount of olive leaves is not specifically limited, and may be such an amount that is unavoidably mixed during harvest. Alternatively, a relatively large amount of leaves may be actively mixed. In view of the properties, especially the antioxidative property, of the extracted olive oil to be produced, the amount of olive leaves is preferably 0.1 to 10% based on the total weight of olive fruits and olive leaves. Note that the olive leaves to be mixed are typically of the same species as that of the olive fruits. However, the olive leaves may be of a different species.

Then, the sorted olive fruits and the olive leaves are lactic fermented. This fermentation is performed by, for example, immersing the olive fruits in a fermentation container filled with saline water, and leaving the fermentation container for a prescribed period. Due to immersion of the olive fruits in the saline water, the olive fruits are gradually lactic fermented, and proceed to decay. This fermentation reduces olive smell of the olive fruits, and can increase fruity smell. As described above, the production method of the present invention is characterized by taking out the olive fruits while the fermentation is in progress, and pressing oil. On the other hand, such a fermentation step does not exist in the conventional olive oil production, and oil is pressed directly from sorted olive fruits.

The time required for fermentation varies depending on the size of the olive fruits, the oil content of the olive fruits, the fermentation temperature, the presence/absence of the saline water and the concentration thereof, the amount of olive leaves, and the like.

Especially, when the saline water concentration is high, the fermentation proceeds at a low rate, and in an extreme case, the fermentation does not proceed eventually. When the saline water concentration is low, on the other hand, the fermentation proceeds at a high rate, and it is therefore preferable to appropriately control the saline water concentration. However, even when the fermentation is performed in normal water without using saline water, the olive fruits doe not proceed to decay for quite a long time in the present invention, and management of the fermentation step is therefore simplified.

The end point of the fermentation can be confirmed by a sense of smell. The fermentation is terminated when olive smell is reduced and fruity smell is strongly sensed. Since the olive fruits are kept firm in the fermentation in the saline water, the external appearance of the olive fruits does not change so much, and it is difficult to visually determine the end point of the fermentation. The fermentation is usually performed in saline water having a concentration of 1 to 10%, and preferably 3 to 5%, and especially 4%. For example, when the fermentation is performed in 4% saline water, the time required for the fermentation is usually about 2 to 4 days.

Moreover, a polystyrene container or the like can be used as the fermentation container, but a wooden container is not preferable since it may be contaminated with germs.

After the fermentation is terminated, the olive fruits and the olive leaves are washed to remove salt derived from the saline water, and are then crushed. Crushing can be performed by a common method, and the olive fruits and the olive leaves become a paste-like matter by crushing.

Next, the paste-like matter is subjected to solid-liquid separation and oil-water separation. The paste-like matter is separated into a solid and a liquid by the solid-liquid separation, and the liquid is separated into water and coarse extracted olive oil by the oil-water separation. If heating is performed in the separations by using means such as distillation, active ingredients contained in the paste-like matter may be decomposed. Therefore, both separations are performed according to a method which does not involve heating, for example, a centrifugation method, a pressing method, or a percolation method.

The coarse extracted olive oil thus obtained is filtered to remove impurities, whereby extracted olive oil is obtained. The filtration is preferably performed by gravity filtration. However, pressure filtration may be performed in order to reduce the filtration time.

The obtained extracted olive oil has no or only slight under-ripe olive smell. Rather, it has sweet and sour fruity smell. Moreover, the obtained extracted olive oil has high skin permeability, and when applied to the skin, is rapidly absorbed without causing stickiness. Moreover, the antioxidative property is very high, and oxidation and degradation of olive oil do not proceed even when the olive oil is left at ordinary temperature or a somewhat high temperature.

An example of performing fermentation after sorting olive fruits was described above. However, the fermentation may be performed at any time before filtration of olive fruits and olive leaves. For example, a paste-like matter resulting from crushing olive fruits and olive leaves may be fermented, or olive fruits and olive leaves may be fermented during crushing.

EXAMPLE

Although the present invention will be described below based on specific examples, the present invention is not limited to these examples.

Example 1: Production of Extracted Olive Oil

Figure 2:
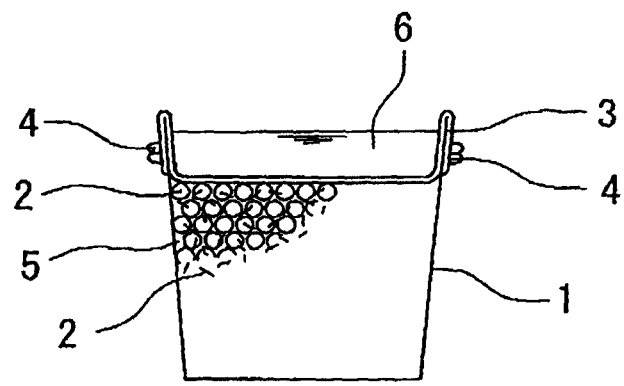
FIG. 2 is a schematic diagram of an apparatus used for fermentation of a first example.

Fermentation of olive fruits and leaves was performed by using an apparatus shown in FIG. 2.

Mission olive fruits were harvested in mid December and sorted, and 30 kg of olive fruits 2 (average fruit weight: 2.7 g; and oil content: 18%) and 1 kg of olive leaves 2' of the same species were placed in a 50 L polystyrene fermentation container 1. 4% of saline water 5 was poured into the fermentation container 1 so that all the olive fruits 2 and the olive leaves 2' were completely immersed. Thereafter, a vinyl sheet 3 was placed over the fermentation container 1, and the vinyl sheet 3 was fixedly fastened to the fermentation container 1 with a rope 4. Then, water 6 is stored on the vinyl sheet 3, a weight is placed thereon, and the fermentation container 1 was left for fermentation. Three days later, it was confirmed that the aroma of olive fruits had changed from olive smell to fruity smell, and the fermentation was terminated at that time.

After the fermentation was terminated, the olive fruits 2 and the olive leaves 2' were washed with water and crushed, and the resultant paste-like matter was centrifugated first for separation into a solid and a liquid, and the obtained liquid was then separated into water and oil. The obtained oil was gravity filtered by using a filter paper having a pore size of 1.5 μm (made by Advantec, Ltd.), whereby 5.1 kg of intended extracted olive oil was obtained. The obtained extracted olive oil had almost no olive smell, and had fruity smell.

Example 2

Similar operation to that of the first example was performed to obtain extracted olive oil, except that the amount of olive leaves of the first example was changed to 0.5 kg. The obtained extracted olive oil had almost no olive smell, and had fruity smell.

Example 3

Similar operation to that of the first example was performed to obtain extracted olive oil, except that the amount of olive leaves of the first example was changed to 3 kg. The obtained extracted olive oil had almost no olive smell, and had fruity smell.

Text Example 1: Evaluation of Stickiness and Skin Permeability

The extracted olive oils obtained in the first to third examples and a normal olive oil produced without fermentation (first comparative example) were applied to the faces of a plurality of subjects to examine the presence or absence of stickiness and the skin permeability.

As a result, regarding the olive oil of the comparative example, all the subjects answered that there was stickiness and the olive oil remained on the skin. Regarding the extracted olive oils of the first to third examples of the present invention, on the other hand, all the subjects answered that there was no stickiness and the olive oil was rapidly absorbed.

Test Example 2: Evaluation of Preservation Stability

The extracted olive oils obtained in the first to third examples, the normal olive oil produced without fermentation (first comparative example), and an extracted olive oil prepared by fermenting only the olive fruits without mixing the olive leaves in the first example (second comparative example) were provided for the preservation stability test.

The result showed that the second comparative example exhibited higher preservation stability than that of the first comparative example, and the first to third examples of the present invention exhibited higher preservation stability than that of the second comparative example.

It is considered that the high preservation stability exhibited by the extracted olive oil produced by the present invention results from dissolving of polyphenols, especially oleuropein, into the olive oil.

What is claimed is:

1. A method for producing extracted olive oil with increased permeability of oleic acid and faster fermentation time, the method comprising:
   crushing olive fruits and olive leaves;
   lactic acid fermenting the olive fruits and the olive leaves before, during or after the crushing step until a predetermined aromatic threshold is reached; and
   producing the extracted olive oil from an obtained paste-like matter,
   wherein the extracted olive oil produced by lactic acid fermenting the olive fruits and the olive leaves before, during or after the crushing step has increased permeability of oleic acid and faster fermentation time compared to olive oil produced from a mixture containing olive oil fruits without olive leaves under similar conditions.

2. The method according to claim 1, wherein the predetermined aromatic threshold is a point at which an olive smell generated by the olive fruits changes to fruity smell.

3. The method according to claim 1, wherein an amount of the olive leaves is 0.1 to 10% based on a total weight of the olive fruits and the olive leaves.

4. The method according to claim 1, wherein the fermentation is performed by immersing the olive fruits and the olive leaves in saline water.

5. The method according to claim 4, wherein the saline water has a salt concentration of 1 to 10%.

6. The method according to claim 1, wherein the extracted olive oil contains dissolved oleuropein.

7. The method according to claim 1, wherein an amount of the olive leaves is 3.2 to 10% based on a total weight of the olive fruits and the olive leaves.

8. The method according to claim 1, wherein an amount of the olive leaves is 5 to 10% based on a total weight of the olive fruits and the olive leaves.

9. The method according to claim 1, wherein the producing of the extracted olive oil comprises subjecting the paste-like matter to solid-liquid separation and oil-water separation.

10. A method for producing extracted olive oil with increased permeability of oleic acid and faster fermentation time, the method comprising:
   crushing olive fruits and olive leaves, an amount of the olive leaves being in the range of 0.1 to 10% based on a total weight of the olive fruits and the olive leaves;
   lactic acid fermenting the olive fruits and the olive leaves before, during or after the crushing step by immersing the olive fruits and the olive leaves in saline water having a salt concentration of 1 to 10%;
   controlling the lactic acid fermentation until a predetermined aromatic threshold is reached; and
   producing the extracted olive oil from an obtained paste-like matter,
   wherein the extracted olive oil produced by lactic acid fermenting the olive fruits and the olive leaves before, during or after the crushing step has increased permeability of oleic acid and faster fermentation time compared to olive oil produced from a mixture containing olive oil fruits without olive leaves under similar conditions.

11. A method for producing extracted olive oil with increased permeability of oleic acid and faster fermentation time, the method comprising:
   controlling the aromaticity of olive fruits by:
      crushing the olive fruits and olive leaves, an amount of the olive leaves being in the range of 0.5 kg to 3 kg;
      lactic acid fermenting the olive fruits and the olive leaves before, during or after the crushing step by:
         immersing the olive fruits and the olive leaves in saline water having a salt concentration of 1 to 10%,
         placing a vinyl sheet over the fermentation container, and
         storing water on the vinyl sheet and placing a weight thereon; and
   producing the extracted olive oil from an obtained paste-like matter,
   wherein the extracted olive oil produced by lactic acid fermenting the olive fruits and the olive leaves before, during or after the crushing step has increased permeability of oleic acid and faster fermentation time compared to olive oil produced from a mixture containing olive oil fruits without olive leaves under similar conditions.

12. The method according to claim 11, wherein the saline water has a salt concentration of 4%.

13. The method according to claim 11, wherein an amount of the olive fruits is 30 kg.

14. The method according to claim 11, wherein an average weight of the olive fruits is 2.7 g, and an oil content of the olive fruits is 18%.

15. The method according to claim 11, wherein the olive fruits and the olive leaves are lactic fermented for about 3 days.

* * * * *